(12) United States Patent
Ohrbom

(10) Patent No.: US 8,008,416 B2
(45) Date of Patent: Aug. 30, 2011

(54) CURABLE ALKOXYCARBONYLAMINO COMPOSITIONS, COATINGS, AND METHODS

(75) Inventor: Walter H. Ohrbom, Hartland Township, MI (US)

(73) Assignee: BASF Coatings GmbH, Muenster (DE)

( * ) Notice: Subject to any disclaimer, the term of this patent is extended or adjusted under 35 U.S.C. 154(b) by 386 days.

(21) Appl. No.: 12/345,237

(22) Filed: Dec. 29, 2008

(65) Prior Publication Data

US 2010/0022719 A1 Jan. 28, 2010

Related U.S. Application Data

(60) Provisional application No. 61/009,633, filed on Dec. 31, 2007.

(51) Int. Cl.
*C08F 26/02* (2006.01)
(52) U.S. Cl. ......... 526/301; 524/198; 524/199; 524/200
(58) Field of Classification Search .................. 526/301; 524/198, 199, 200
See application file for complete search history.

(56) References Cited

U.S. PATENT DOCUMENTS

| 4,608,420 | A | 8/1986 | Brindoepke et al. |
| 5,504,242 | A | 4/1996 | Yabuta et al. |
| 5,627,240 | A | 5/1997 | Furukawa et al. |
| 5,892,100 | A | 4/1999 | Yamanaka et al. |
| 6,121,446 | A | 9/2000 | Flood |
| 6,506,898 | B1 | 1/2003 | Flood et al. |
| 7,371,856 | B2 | 5/2008 | Schneider et al. |
| 2004/0087747 | A1 | 5/2004 | Ohrbom et al. |

FOREIGN PATENT DOCUMENTS

| DE | 195 23 175 | 1/1997 |
| EP | 0 468 643 | 1/1992 |
| EP | 0 680 982 | 11/1995 |
| EP | 0 680 994 | 11/1995 |
| EP | 0 915 113 | 5/1999 |
| FR | 2 728 567 | 6/1996 |
| WO | WO 2006/009443 | 1/2006 |
| WO | WO 2007/037858 | 4/2007 |

OTHER PUBLICATIONS

Kanamaru, N., et al., "Polyaddition Reaction Using Bifunctional Acylisocyanates", Polymer Preprints. Japan, Society of Polymer Science, JP, vol. 42, No. 6, (Jan. 1, 1993), pp. 1992-1924, XP009044021.
International Search Report and Written Opinion for Application PCT/US2008/088460 mailed Dec. 30, 2009.

*Primary Examiner* — Edward J Cain
(74) *Attorney, Agent, or Firm* — Harness, Dickey & Pierce, P.L.C.

(57) ABSTRACT

A compound, oligomer, or polymer having a functional group of formula (I)

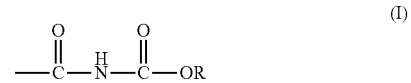

wherein R is a group having 1 to 12 carbons and optionally including one or more heteroatoms selected from oxygen, nitrogen, and sulfur is useful in curable compositions having active hydrogen functional groups reactive with group (I). The functional groups of formula (I) and active hydrogen functional groups may be part of the same material or different materials. In some embodiments a filler is surface modified to have a functional group of formula (I). Also disclosed is a method of making a material having a functional group of formula (I).

9 Claims, No Drawings

CURABLE ALKOXYCARBONYLAMINO COMPOSITIONS, COATINGS, AND METHODS

CROSS-REFERENCE TO RELATED APPLICATIONS

This application claims the benefit of U.S. Provisional Application No. 61/009,633 filed on Dec. 31, 2007, the entire disclosure of which is incorporated herein by reference.

FIELD OF THE DISCLOSURE

This invention relates to alkoxycarbonylamino materials, curable compositions containing such materials, particularly coating compositions, and related methods.

BACKGROUND OF THE DISCLOSURE

The statements in this section merely provide background information related to this disclosure and may not constitute prior art.

Derivatives of amino-1,3,5-triazines have been widely used as crosslinking agents in curable compositions, but their use has not been without concerns. For example, alkoxylated melamine formaldehyde resins suffer from the drawback of releasing formaldehyde as a volatile by-product of the curing process. In many applications the derivatives of amino-1,3,5-triazines have been replaced by triazine carbamates (also known as carbamate functional 1,3,5 triazine), including tris (alkoxy carbonylamino) triazine (TACT); see for example Flood et al., U.S. Pat. No. 6,506,898. The triazine carbamates are reactive with a range of oligomers and polymers having an epoxy group and/or an active hydrogen group. However, the triazine carbamates have limited solubility in many organic solvents. Accordingly, dilute solutions of the triazine carbamates must be used resulting in a less than desirable volatile organic content (VOC) in a coating composition. Additionally, there is some concern with regard to the environmental impact of triazine carbamates.

Accordingly, there remains a need in the art for curable compositions which release little or no formaldehyde or other volatile compound during curing.

SUMMARY OF THE DISCLOSURE

The above-discussed and other drawbacks and deficiencies of the prior art are overcome or alleviated by a material that is a compound, oligomer, or polymer having a functional group (I)

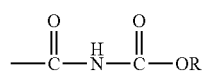

(I)

wherein R is a group having 1 to 12 carbons and optionally including one or more heteroatoms selected from oxygen, nitrogen, and sulfur. The material can be used in curable compositions, including coating compositions, in combination with a compound, oligomer, or polymer having a functional group with active hydrogen functionality. In some embodiments a single material comprises a first functional group of formula (I) and a second functional group having an active hydrogen. In certain embodiments, the functional group (I) is bonded to an electronegative atom, such as an oxygen atom, a sulfur atom, or a nitrogen atom. In various embodiments, the material has one or more groups of formula (I) and one or more carbonylamine groups (II):

(II)

Also disclosed herein are methods of making a compound having a functional group of formula (I).

Oligomers are polymers having relatively few monomer units; generally, "oligomer" refers to polymers with ten or fewer monomer units. "Compounds" will refer to nonpolymeric materials; that is, to materials that do not have two or more repeating monomer units. The molecular weight of a material may be determined by gel permeation chromatography (GPC), particularly by using polysytrene standards when the material is an oligomer or polymer.

Compounds having a functional group of formula (I) have a reactivity similar to that of triazine carbamates but can reduce or eliminate the drawbacks of the triazine carbamates. For example, the compound comprising the functional group (I) can be a polymer or oligomer tailored to address solubility issues, for example by comonomer selection, incorporating ionic groups to improve dispersibility in aqueous conditions, limiting overall molecular size, and the like. Including group (I) allows a wide range of flexibility in molecular design for curable compositions and particularly allows a wide range of flexibility in coating system design.

For convenience, "resin" is used in this disclosure to encompass resin, oligomer, and polymer, and "binder" refers to the film-forming components of the coating composition. "A," "an," "the," "at least one," and "one or more" are used interchangeably to indicate that at least one of the item is present; a plurality of such items may be present. Other than in the working examples provides at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range.

The above-discussed and other features and advantages of the present invention will be appreciated and understood by those skilled in the art from the following detailed description. Further areas of applicability will become apparent from the description provided herein. It should be understood that the description and specific examples are intended for purposes of illustration only and are not intended to limit the scope of the present disclosure.

DETAILED DESCRIPTION

The curable compositions include a material that is a compound, oligomer, or polymer having a functional group (I)

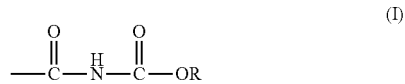
(I)

wherein R is a group having 1 to 12 carbons and optionally including one or more heteroatoms selected from oxygen, nitrogen, and sulfur. In some embodiments R has 1 to 8 carbons, or, more specifically, 1 to 4 carbons. R can be saturated, or unsaturated, straight-chain, cyclic, or branched aliphatic; aromatic; or combinations, i.e., alkylaryl or arylalkyl. In particular embodiments, R comprises a heteroatom as part of group selected from carbonyl groups, carboxylic acid groups, ester groups, amino groups, amide groups, hydroxyl groups, alkoxyl groups, halo groups, nitro groups, cyano groups, sulfonyl groups, sulfoxyl groups, sulonamide groups, sulfamoyl groups, and combinations of these. It will be appreciated that certain of these heteroatom groups (e.g., hydroxyl groups) potentially are reactive with functional group (I) itself. Certain heteroatom groups may be provided to the R group by adduction or conversion of another group after the alkoxy carbonylamino group has been formed. In various embodiments, the group (I) may be directly bonded to an electronegative atom such as an oxygen atom, a nitrogen atom, or a sulfur atom so that the compound, oligomer, or polymer has one of functional groups (III) to (V):

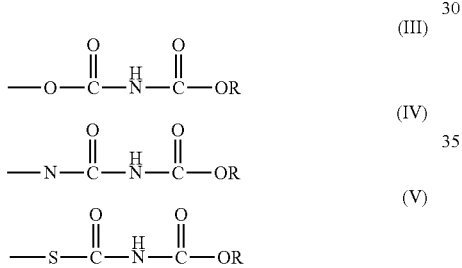
(III)
(IV)
(V)

wherein R is as previously defined.

The material comprising the functional group of formula (I) can be a compound, oligomer, or polymer. The compound, oligomer, or polymer can comprise (and advantageously does comprise) more than one functional group of formula (I). For example, the compound, oligomer or polymer can comprise 2 to 8 functional groups of formula (I). In some embodiments the oligomer or polymer comprises other functional groups connected to the backbone of the oligomer or polymer in addition to the functional group of formula (I). When other functional groups are present they can be non-reactive with the functional group of formula (I) or they can be reactive with the functional group of formula (I). When the additional functional groups are reactive with the functional group of formula (I) the polymer or oligomer can be described as "self crosslinking" meaning that the additional groups react with the functional groups of formula (I) under cure conditions to form a crosslinked network. Groups reactive with isocyanate (—NCO) are reactive with the functional groups of formula (I). Exemplary functional groups reactive with the functional group of formula (I) are epoxide and groups having an active hydrogen such as hydroxyl groups, thio groups, amine groups, and the like.

In one particular embodiment, the compound, oligomer, or polymer having functional groups of formula (I) also has one or more carbamate groups of formula (II):

(II)

The material comprising a functional group (I) may be prepared by various methods. In general, the material may be prepared either by adducting a pre-formed compound, oligomer, or polymer with the group (I) or by adducting a precursor for the compound, oligomer, or polymer with the group (I) and then making further modifications to the adduct to produce the compound, oligomer, or polymer with the group (I). As an instance of the second general method, a monomer may be adducted with the group (I) and the adduct monomer then polymerized to produce an oligomer or polymer with the group (I). Particular methods for preparing a compound, oligomer, or polymer with the group (I) follow in which reference is made to adducting primary carbamate groups

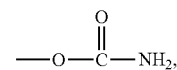

although the methods in general apply as well to groups selected from primary amide

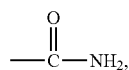

primary urea

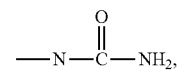

and primary thiourea

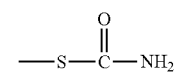

groups.

In general, the material comprising a functional group of formula (I) can be made by reacting a material (compound, oligomer, or polymer with a group or groups of formula (II):

(II)

(such as the mentioned primary carbamate, primary amide, primary urea, and primary thiourea groups) via the known synthetic processes that have been used to prepare alkoxycarbonylamino-1,3,5-triazine compounds, including those described in Schneider et al, U.S. Pat. No. 7,371,856 and Flood, U.S. Pat. Nos. 6,506,898 and 6,121,446.

In one method, the material comprising a functional group of formula (I) can be made by reacting a material (compound, oligomer, or polymer with a group or groups of formula (II):

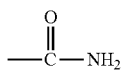

(II)

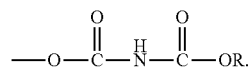

(III)

with carbon monoxide and an alcohol, R—OH at suitable temperatures, and, depending on the starting components, nearly complete conversion can occur between 2 hours and 24 hours. When the starting material has a plurality of groups (I) the reaction may be stopped at a desired point before completion to provide a material with mixed functionality of both formulas (I) and (II). The components can be reacted either by a batch or continuous flow system. In some embodiments, the reaction is done in a batch reactor, such as an autoclave.

The carbon monoxide can be pure carbon monoxide or may contain other gases or "impurities", such as, for example, nitrogen, argon, helium, carbon dioxide, oxygen, air, a hydrocarbon, or a halogenated hydrocarbon. Generally, any commercially available carbon monoxide may be utilized. In some embodiments the carbon monoxide is substantially free of water.

In another method, the material comprising a functional group of formula (I) can be made by reacting a material (compound, oligomer, or polymer with a group or groups of formula (II):

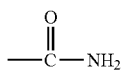

(II)

with dimethyl carbonate and ROH, wherein R is as previously defined with the proviso that any heteroatoms present are one or two ether oxygen atoms, in the presence of an alkali metal methoxide or an alkaline earth metal methoxide. The dimethyl carbonate is generally used in amounts from 0.1 to 10 moles, preferably from 1 to 3 moles per mole of carbonylamino groups. The alcohol may be, for example, ethanol, propanol, isopropanol, butanol, isobutanol, sec-butanol, tert-butanol, 2-methoxyethanol, 2-ethoxyethanol, 3-methoxypropanol, and so on. Different alcohols may be used in any combination. The alcohol is generally used in up to a 50 times molar excess relative to the carbonylamino groups, preferably from 3 to 30 moles per mole of carbonylamino groups. Examples of suitable alkali metal or alkaline earth metal methoxides include, without limitation, lithium, sodium, potassium, magnesium, and calcium methoxides and may be used in amounts from 0.1 to 10 moles, preferably from 1 to 3 moles per mole of carbonylamino groups. The methoxides may be used in combinations if desired, and may be used either in solid aggregate state or dissolved or suspended in the reaction medium. The alcohols are useful reaction media, but inert solvents and diluents may be used instead of or in combination with alcohols. Catalysts such as lithium chloride, magnesium chloride, or sodium carbonate may be used.

The reaction may be carried out at a temperature from 20 to 180° C., typically under atmospheric pressure, but the pressure may generally be up to 8 bar.

In various embodiments of these methods, the carbonyl amino groups have structure In these embodiments, the reaction may be stopped after a desired degree of completion to provide an adduct having groups of both structure (I) and structure (II).

Nonlimiting examples of compounds having groups (II) include carbamate ethyl (meth)acrylate, carbamate propyl (meth)acrylate, 1-carbamate-2-ethylhexane, dicarbamate,diethyloctane, and the dicarbamate of dimerized fatty acid. As used in this description, "(meth)acrylate" refers to both the acrylate and methacrylate compounds. When the compound having group (I) has a polymerizable group or polymerizable groups, for example a compound prepared using carbamate ethyl (meth)acrylate or carbamate propyl (meth)acrylate having structures

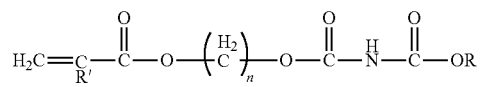

with R' being H or methyl, n being 2 or 3, and R being as previously defined that has polymerizable ethylenic group, it may be polymerized, optionally with comonomers, to prepare an oligomer or polymer having groups (I).

An oligomer or polymer comprising a functional group of formula (I) can comprise one or more types of repeating structural units. Exemplary repeating structural units include urethanes, amides, esters, aliphatic, aromatic ethers, and combinations comprising one or more of the foregoing. Nonlimiting examples of oligomers and polymers having functional groups (I) include vinyl polymers such as acrylic polymers, polyurethanes, polyesters, polyethers, epoxies, polyamides, polycarbonates, and so on, as well as graft and block polymers having combinations of these. One type of oligomer is a so-called "star" polymer prepared using a hyperbranched core.

The oligomer or polymer comprising a functional group of formula (I) can be prepared by adducting an oligomer or polymer having primary carbamate groups (II) to convert those groups to groups (III).

In one example, the polymer that is adducted is an acrylic polymer comprising primary carbamate groups. The carbamate groups may be introduced to the polymer by either polymerizing using a carbamate-functional monomer or by reacting a functional group on the formed polymer in a further reaction to produce a carbamate group at that position. If the functional group on the acrylic polymer (b) is an isocyanate group, the isocyanate group can be reacted with a hydroxyalkyl carbamate, or with a hydroxy-containing epoxide with the epoxy group subsequently converted to carbamate by reaction with $CO_2$ and then ammonia. Preferably, an isocyanate-functional acrylic polymer is reacted with hydroxyethyl carbamate, hydroxypropyl carbamate, hydroxybutyl carbamate, or mixtures thereof. If the functional group is hydroxyl, the reactive group on the carbamate-containing compound may be oxygen of the C(=O)—O portion of the carbamate group on an alkyl carbamate or methylol, such as with methylol acrylamide (HO—$CH_2$—NH—C(=O)—CH=$CH_2$). In the case of the C(=O)—O group on an alkyl carbamate, the hydroxyl group on the polymer undergoes a transesterification with the C(=O)—O group, resulting in the carbamate group being appended to the polymer. In the case of methylol acrylamide, the unsaturated double bond is then reacted with peroxide to convert to an epoxy group, then $CO_2$, to form a cyclic carbonate, and then with ammonia or a primary amine to form the carbamate. If the functional group on the polymer is a carboxyl group, the carboxyl group can be reacted with epichlorohydrin to form a monoglycidyl ester, which can be converted to carbamate by reaction with $CO_2$, and then ammonia.

Carbamate functionality can also be introduced to an acrylic polymer by reacting the polymer with a compound that has a group that can be converted to a carbamate, and then converting that group to the carbamate. Examples of suitable compounds with groups that can be converted to a carbamate include, without limitation, active hydrogen-containing cyclic carbonate compounds (e.g., the reaction product of glycidol and $CO_2$) that are convertible to carbamate by reaction with ammonia, monoglycidyl ethers and esters convertible to carbamate by reaction with $CO_2$ and then ammonia, allyl alcohols where the alcohol group is reactive with isocyanate functionality and the double bond can be converted to carbamate by reaction with peroxide, and vinyl esters where the ester group is reactive with isocyanate functionality and the vinyl group can be converted to carbamate by reaction with peroxide, then $CO_2$, and then ammonia. Any of the above compounds can be utilized as compounds containing carbamate groups rather than groups convertible to carbamate by converting the group to carbamate prior to reaction with the polymer.

Such polymers can be prepared from ethylenically unsaturated monomers having at least one carbon-carbon double bond able to undergo free radical polymerization. Illustrative ethylenically unsaturated monomers include, without limitation, alpha, beta-ethylenically unsaturated monocarboxylic acids containing 3 to 5 carbon atoms such as acrylic, methacrylic, and crotonic acids, and the esters, nitriles, and amides of those acids; alpha, beta-ethylenically unsaturated dicarboxylic acids containing 4 to 6 carbon atoms and the anhydrides, monoesters, and diesters of those acids; vinyl esters, vinyl ethers, vinyl ketones, and aromatic or heterocyclic aliphatic vinyl compounds. Carbamate-functional ethylenically unsaturated monomers, cyclic carbonate functional ethylenically unsaturated monomers, and/or isocyanate functional ethylenically unsaturated monomers may also be used, most preferably in combination with other ethylenically unsaturated monomers. Representative examples of suitable esters of acrylic methacrylic, and crotonic acids include, without limitation, those esters from reaction with saturated aliphatic and cycloaliphatic alcohols containing 1 to 20 carbon atoms, such as methyl, ethyl, propyl, isopropyl, n-butyl, isobutyl, tert-butyl, 2-ethylhexyl, lauryl, stearyl, cycolhexyl, trimethylcyclohexyl, tetrahydrofurfuryl, stearyl, sulfoethyl, and isobornyl acrylates, methacrylates, and crotonates; and polyalkylene glycol acrylates and methacrylates. The functional group can be incorporated into the ester portion of the acrylic monomer. For example, hydroxy-functional acrylic monomers that can be used to form such polymers include hydroxyethyl acrylate, hydroxybutyl acrylate, hydroxybutyl methacrylate, hydroxypropyl acrylate, and the like; amino-functional acrylic monomers would include t-butylaminoethyl methacrylate and t-butylamino-ethylacrylate; acid-functional monomers would include acrylic acid, methacrylic acid, and itaconic acid; epoxide-functional monomers would include glycidyl acrylate and glycidyl methacrylate; ethylenically unsaturated isocyanate monomers such as meta-isopropenyl-$\alpha,\alpha$-dimethylbenzyl isocyanate (sold by American Cyanamid as TMI®) and isocyanato-ethyl methacrylate. Cyclic carbonate ethylenically unsaturated monomers are well-known in the art and include (2-oxo-1,3-dioxolan-4-yl)methyl methacrylate. Representative examples of other ethylenically unsaturated polymerizable monomers include, without limitation, such compounds as fumaric, maleic, and itaconic anhydrides, monoesters, and diesters with alcohols such as methanol, ethanol, propanol, isopropanol, butanol, isobutanol, and tert-butanol. Representative examples of polymerizable vinyl monomers include, without limitation, such compounds as vinyl acetate, vinyl propionate, vinyl ethers such as vinyl ethyl ether, vinyl and vinylidene halides, and vinyl ethyl ketone. Representative examples of aromatic or heterocylic aliphatic vinyl compounds include, without limitation, such compounds as styrene, alpha-methyl styrene, vinyl toluene, tert-butyl styrene, and 2-vinyl pyrrolidone. Representative examples include acrylic and methacrylic acid amides and aminoalkyl amides, acrylonitrile, and methacrylonitriles.

One way to prepare carbamate functional acrylic polymers is to prepare an acrylic monomer having a carbamate functionality in the ester portion of the monomer. Such monomers are well-known in the art and are described, for example in U.S. Pat. Nos. 3,479,328, 3,674,838, 4,126,747, 4,279,833, and 4,340,497, 5,356,669, and WO 94/10211, the disclosures of which are incorporated herein by reference. One method of synthesis involves reaction of a hydroxy-functional monomer with cyanic acid (which may be formed by the thermal decomposition of urea) to form the carbamyloxy carboxylate (i.e., carbamate-modified (meth)acrylate). Another method of synthesis reacts an alpha,beta-unsaturated acid ester with a hydroxy carbamate ester to form the carbamyloxy carboxylate. Yet another technique involves formation of a hydroxyalkyl carbamate by reacting a primary or secondary amine or diamine with a cyclic carbonate such as ethylene carbonate. The hydroxyl group on the hydroxyalkyl carbamate is then esterified by reaction with acrylic or methacrylic acid to form the monomer. Other methods of preparing carbamate-modified acrylic monomers are described in the art, and can be utilized as well. The acrylic monomer can then be polymerized along with other ethylenically-unsaturated monomers, if desired, by techniques well-known in the art.

An alternative route for preparing a carbamate-functional acrylic polymer is to react an already-formed polymer such as an acrylic polymer with another component to form a carbamate-functional group appended to the polymer backbone, as described in U.S. Pat. No. 4,758,632, the disclosure of which is incorporated herein by reference. One technique for preparing acrylic polymers useful as the second component involves thermally decomposing urea (to give off ammonia and HNCO) in the presence of a hydroxy-functional acrylic polymer to form a carbamate-functional acrylic polymer. Another technique involves reacting the hydroxyl group of a hydroxyalkyl carbamate with the isocyanate group of an isocyanate-functional acrylic or vinyl monomer to form the carbamate-functional acrylic. Isocyanate-functional acrylics are known in the art and are described, for example in U.S. Pat. No. 4,301,257, the disclosure of which is incorporated herein by reference. Isocyanate vinyl monomers are well-known in the art and include unsaturated m-tetramethyl xylene isocyanate and isocyanatoethyl methacrylate. Yet another technique is to react the cyclic carbonate group on a cyclic carbonate-functional acrylic with ammonia in order to form the carbamate-functional acrylic. Cyclic carbonate-functional acrylic polymers are known in the art and are described, for example, in U.S. Pat. No. 2,979,514, the disclosure of which is incorporated herein by reference. Another technique is to transcarbamylate a hydroxy-functional acrylic polymer with an alkyl carbamate. A more difficult, but feasible way of preparing the polymer would be to transesterify an acrylate polymer with a hydroxyalkyl carbamate.

The primary carbamate groups of the acrylic polymer are then converted to the groups of structure (III), for example via one of the processes outlined above.

Polyurethanes, polyesters, polyethers, polyamides, polycarbonates, and epoxy resins can be prepared similarly by preparing such polymers or oligomers with primary carbamate, primary amide, primary urea, and/or primary thiourea groups, then converting those groups to functional groups of formula (I), or by preparing such polymers or oligomers using a monomer comprising one or more functional groups of formula (I).

In one embodiment, the material is a hyperbranched, functional material prepared by a step of reacting an epoxy group with a carboxylic acid group and converting the resulting hydroxyl group to a carbamate group by one of the methods described already or known in the art. In particular, the hyperbranched functional material is a carbamate-functional resin having in its structure a hyperbranched or star polyol core, a first chain extension based on a polycarboxylic acid or cyclic anhydride, a second chain extension based on an epoxide-containing compound, and having carbamate functional groups on the core, the second chain extension, or both. Such a hyperbranched compound, then, has a residue of the polyol as its core, a residue of the polycarboxylic acid or cyclic anhydride as its first extension, and a residue of the epoxide as its next extension. Because each epoxide ring may open at the inner or the outer carbon, such a reaction product will be a mixture of isomers.

A carbamate-functional resin based on a star or hyperbranched core with carbamate functionality may be prepared by introducing onto the core by reacting the core with a compound containing a carbamate group and a functional group reactive with the hydroxyl groups on the core. Alternatively, it can be introduced by a series of extension steps with a polycarboxylic acid or anhydride and epoxy compound, followed by carbamoylation. The star core may be a structure based on a star polyol. A star polyol is a monomeric polyol containing three or more primary or secondary hydroxyl groups. In a preferred embodiment, the star polyol has four or more hydroxyl groups. Examples of star polyols include, without limitation, glycerol, trimethylolpropane, trimethylolethane, pentaerythritol, ditrimethylolpropane, dipentaerythritol, tetrakis(2-hydroxyethyl)methane, diglycerol, trimethylolethane, xylitol, glucitol, dulcitol, and sucrose. Mixtures of star polyols may also form the star core of the carbamate-functional resin.

A hyperbranched core is a structure based on hyperbranched polyols. Hyperbranched polyols are prepared by the reaction of a first compound having two or more hydroxyl groups and a second compound having one carboxyl group and two or more hydroxyl groups. The first and second compounds can be reacted to form a first generation hyperbranched polyol. Alternatively, the second compound can be reacted with the first generation hyperbranched polyol to form a second generation and, if desired, subsequent generations. Preferably, a first generation or second generation hyperbranched polyol is used as the hyperbranched core of the carbamate-functional resin.

The first compound can suitably be an aliphatic, a cycloaliphatic, or an aromatic diol, triol, or tetrol, a sugar alcohol such as sorbitol and mannitol, dipentaerythritol, an α-alkylglucoside such as α-methylgucoside, or an alkoxylate polymer having a molecular weight of at most about 8,000 that is produced by a reaction between an alkylene oxide or a derivative thereof and one or more hydroxyl groups from any of the alcohols mentioned above. Mixtures of these can also be used as the first compound. Diols suitable as the first compound include straight diols with 2-18 carbon atoms. Examples include, without limitation, 1,3-propanediol, 1,2-ethanediol, 1,4-butanediol, 1,5-pentanediol, and 1,6-hexanediol. The diols can also be branched such as, for instance, dimethylolpropane, neopentyl glycol, 2-propyl-2-methyl-1,3-propanediol, 2-butyl-2-ethyl-1,3-propanediol, 2,2-diethyl-1,3-propanediol, 2,2,4-trimethylpentane-1,3-diol, trimethylhexane-1,6-diol, and 2-methyl-1,3-propanediol. Other suitable diols include, without limitation, diethylene glycol, triethylene glycol, polyethylene glycols, dipropylene glycol, tripropylene glycol and polypropylene glycols. Cycloaliphatic diols such as cyclohexane dimethanol and cyclic formals of pentaerythritol such as, for instance, 1,3-dioxane-5,5-dimethanol can also be used. Aromatic diols, for instance 1,4-xylylene glycol and 1-phenyl-1,2-ethanediol, as well as reaction products of polyfunctional phenolic compounds and alyklene oxides or derivatives thereof, can furthermore be employed. Bisphenol A, hydroquinone, and resorcinol may also be used. Diols of the ester type, for example neopentylhydroxypivalate, are also suitable diols. As substitute for a 1,2-diol, the corresponding 1,2-epoxide or an α-olefin oxide can be used. Ethylene oxide, proplyene oxide, 1,2-butylene oxide, and styrene oxide can serve as examples of such compounds. Suitable triols can contain three primary hydroxyl groups. Trimethylolpropane, trimethylolethane, trimethylobutane, and 3,5,5-trimethyl-2,2-dihydroxymethylhexane-1-ol are examples of this type of triols. Other suitable triols are those having two types of hydroxyl groups, primary as well as secondary hydroxyl groups, as for instance glycerol and 1,2,6-hexanetriol. It is also possible to use cycloaliphatic and aromatic triols and/or corresponding adducts with alkylene oxides or derivatives thereof. Suitable tetrols for use as the first coGGmpound include, without limitation, pentaerythritol, ditrimethylolpropane, diglycerol and ditrimethylolethane. It is also possible to use cycloaliphatic and aromatic tetrols as well as corresponding adducts with alkylene oxides or derivatives thereof.

The second compound used to prepare the hyperbranched polyol can be a monofunctional carboxylic acid having at least two hydroxyl groups. Examples include, without limitation α,α-bis(hydroxymethyl)propionic acid (dimethylol propionic acid), α,α-bis(hydroxymethyl)butyric acid, α,α,α-tris(hydroxymethyl)acetic acid, .α,α-bis(hydroxymethyl)valeric acid, α,α-bis(hydroxyethyl)propionic acid or α-phenyl-carboxylic acids having at least two hydroxyl groups directly pendant to the phenyl ring (phenolic hydroxyl groups) such as 3,5-dihydroxybenzoic acid.

The hyperbranched polyols can be prepared by reacting the first compound and second compound under esterification conditions. The temperature of reaction is generally from 0 to 300° C., preferably 50 to 280° C., and most preferably 100 to 250° C. A first generation intermediate is prepared by reacting the first compound and second compound in an equivalent molar ratio of hydroxyls on the first compound to carboxyl groups on the second compound of between about 1:2 and about 2:1. Preferably the equivalent ratio will be from about 1:1.5 to about 1.5:1, and even more preferably from about 1:1.2 to about 1.2:1. The functionality and polydispersity of the first generation intermediate, and of any subsequent generation, depend on the equivalent ratio of hydroxyl groups to carboxyl groups of the reactants in each step. The functionality of the hyperbranched polyol, whether first generation or subsequent generation, should be four hydroxyl groups or greater. Hyperbranched polyols with a wide range of polydispersities are useful. It is preferred that the polydispersity be less than about 2.5, preferably less than about 2.0, and most preferably less than about 1.8.

The core polyol, either star or hyperbranched as described above, is next reacted with a polycarboxylic acid or anhydride to form a first chain extension containing an ester linkage and a free carboxyl group. Preferred as the polycarboxylic acid or anhydride are cyclic carboxylic anhydrides. Anhydrides are advantageous for this step because the ring-opening esterification is faster than reaction of remaining hydroxyl groups on the core polyol with the carboxyl group liberated by the ring opening reaction. As a consequence the first chain extension is a half acid ester with little polymerization or polyester formation. Suitable anhydrides include, without limitation, anhydrides of dicarboxylic acids with carboxyl groups on adjacent carbons. The anhydrides can be aliphatic, cycloaliphatic, or aromatic. Examples include without limitation, maleic anhydride, succinic anhydride, phthlalic anhydride, hexahydrophthalic anhydride, tetrahydrophthalic anhydride, methyl tetrahydrophthalic anhydride, methylhexahydrophthalic anhydride, and trimellitic anhydride. Other anhydrides useful in the invention include, without limitation, adipic anhydride, glutaric anhydride, malonic anhydride, and the like. The reaction of the polycarboxylic acid or anhydride with the core polyol results in formation of a first intermediate that has carboxyl functionality and may contain some primary or secondary hydroxyl groups that result from any unreacted hydroxyl groups on the core polyol. The stoichiometry is chosen so that at least one primary hydroxyl group of the core polyol reacts with the polycarboxylic acid or anhydride. Preferably at least two hydroxyl groups on the core polyol will be reacted. In some embodiments the molar ratio of hydroxyl on the core polyol to carboxyl group on the polycarboxylic acid or anhydride will be approximately 1:1, so that essentially every hydroxyl group on the core polyol is esterified.

The first intermediate, which contains at least one carboxyl group and optionally has primary or secondary hydroxyl groups as noted above, is next reacted with a compound containing an epoxide group to form a second intermediate having a chain extension based on a glycidyl ester of a neo-acid such as, without limitation, neodecanoic or neononanoic acid, or a glycidyl ester of a mixture of fatty acids, or a combinations of these. The reaction of the epoxide compound with the first intermediate is preferably carried out without catalyst. In this case, the epoxide group of the epoxide-containing compound reacts faster with the carboxyl group than with any primary or secondary hydroxyl groups that may be present on the first intermediate. Therefore, a relatively clean chain extension is achieved to form a second intermediate that contains secondary hydroxyl groups resulting from ring opening of the epoxide, as well as any primary or secondary hydroxyl groups that remained unreacted in the formation of the first intermediate. Reaction conditions are selected to allow the epoxide group to open in either direction, resulting in a mixture of products, following reaction conditions known in the art. Preferably the epoxy containing compound is reacted in a molar ratio of about 1:1 with respect to carboxyl groups on the first intermediate. However, if carboxyl groups are desired in the final product (for example for salting with amines to provide a water dispersible coating), an excess of carboxyl functional first intermediate may be used.

To make the resin having groups (II), specifically primary carbamate groups

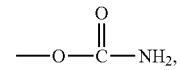

for example, a carbamate group may be added to the second intermediate by reacting the second intermediate with phosgene and then ammonia to form a compound having primary carbamate groups, or by reaction of the second intermediate with phosgene and then a primary amine to form a compound having secondary carbamate groups. Alternatively, the second intermediate may be reacted with one or more ureas to form a compound with secondary carbamate groups (i.e., N-alkyl carbamates). This reaction is accomplished by heating a mixture of the second intermediate and urea. Another technique is the reaction of the second intermediate with a monoisocyanate, for example methylisocyanate, to form a compound with secondary carbamate groups. In another example, the second intermediate can be reacted with cyanic acid formed by the thermal decomposition of urea, or reacted with a compound having a carbamate group capable of undergoing a transesterification with the hydroxyl groups on the second intermediate. These include, without limitation, methyl carbamate, butyl carbamate, propyl carbamate, 2-ethylhexyl carbamate, cyclohexyl carbamate, phenyl carbamate, hydroxypropyl carbamate, hydroxyethyl carbamate, and the like. The transesterification reaction between the second intermediate and the carbamate compound can be conducted under typical transesterification conditions, as described above. The primary carbamate groups of the hyperbranched or star oligomer are then converted to the groups of structure (III), for example via one of the processes outlined above.

In some embodiments the oligomer or polymer comprising a functional group of formula (I) also comprises functional groups curable by actinic radiations. As used herein, actinic radiation means electromagnetic radiation, such as near infrared (NIR), visible light, UV radiation or X-rays, especially UV radiation, and corpuscular radiation, such as electron beams. Exemplary groups include those having a bond which on exposure to actinic radiation becomes reactive and, with other activated bonds of its kind, enters into polymerization reactions and/or crosslinking reactions which proceed in accordance with free-radical and/or ionic mechanisms. Examples of suitable bonds include carbon-hydrogen single bonds or carbon-carbon, carbon-oxygen, carbon-nitrogen, carbon-phosphorus or carbon-silicon single bonds or double bonds. Of these, the carbon-carbon double bonds are particularly advantageous. For the sake of brevity, they are referred to below as "double bonds". If more than one double bond is used, the double bonds may be conjugated but in some embodiments it is of advantage if the double bonds are present in isolation, in particular each being present terminally, in the group in question.

If on average per molecule more than one group which can be activated with actinic radiation is employed, the groups are structurally different from one another or are of the same structure. If they are structurally different from one another, this means that use is made of two, three, four or more, but especially two, groups which can be activated with actinic radiation, which are derived from two, three, four or more, but especially two, monomer classes. Examples of suitable groups include (meth)acrylate, ethacrylate, crotonate, cinnamate, vinyl ether, vinyl ester, dicyclopentadienyl, norbornenyl, isoprenyl, isopropenyl, allyl or butenyl groups; dicyclopentadienyl ether, norbornenyl ether, isoprenyl ether, isopropenyl ether, allyl ether or butenyl ether groups; or dicyclopentadienyl ester, norbornenyl ester, isoprenyl ester, isopropenyl ester, allyl ester or butenyl ester groups, but especially acrylate groups. The groups can be attached to the respective parent structures of the oligomer or polymer via urethane, urea, allophanate, ester, ether and/or amide groups, but in particular via ester groups. Normally, this occurs as a result of customary and known polymer-analogous reactions such as, for instance, the reaction of lateral glycidyl groups with olefinically unsaturated monomers that contain an acid group, of lateral hydroxyl groups with the halides of these monomers, of hydroxyl groups with isocyanates containing double bonds such as vinyl isocyanate, methacryloyl isocyanate and/or 1-(1-isocyanato-1-methylethyl)-3-(1-methylethenyl)benzene (TMI® from CYTEC), or of isocyanate groups with the hydroxyl-containing monomers described above.

Curable compositions, particularly coating compositions, include a material comprising functional groups of formula (I) with either the same material or a second material comprising functional groups reactive under curing conditions with the functional groups of formula (I). When the same material comprises both the functional groups of formula (I) and those groups reactive under cure conditions with the groups of formula (I), then the material is said to be self-crosslinking. In some embodiments the functional groups reactive under curing conditions with the functional groups of formula (I) are active hydrogen groups. In some embodiments the material having an active hydrogen groups functions as a cross linking agent. In one embodiment, the curable material comprises functional groups of formula (III) having a hydroxyl group on a carbon atom beta to the carbon atom to which the group of formula (III) is attached.

The polymers, oligomers, or compounds having groups (I) may incorporated into coating compositions, particularly thermosetting coating compositions. Such coating compositions may be used to coat automotive and industrial substrates. The industrial and automotive coatings may be primers or topcoats, including one-layer topcoats and basecoat/clearcoat composite coatings. Suitable examples of functionality reactive with crosslinkers that may be included are, without limitation, epoxide groups, active hydrogen-containing functional groups such as carbamate groups, terminal urea groups, hydroxyls, amines, thiols, and activated methylene groups such as those having the structure

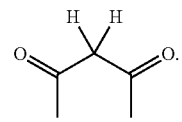

These groups may be used in combinations. The crosslinkable materials having such active hydrogen groups may be compounds, oligomers, or polymers. In certain embodiments, at least one of (a) the material having groups (I) and (b) the crosslinkable materials having such active hydrogen groups has least three of such functional groups and the other one (a) and (b) has at least two of such functional groups, on average, per molecule.

Nonlimiting examples of materials that having active hydrogen groups include vinyl polymers such as acrylic polymers, polyesters, polyurethanes, polyethers, and nonpolymeric materials such as esters, functional alkanes, dimmer fatty acids and derivatives of dimer fatty acid, and the like having any of the active hydrogen-containing functional groups already mentioned.

The coating compositions may further include other customary materials, including pigments, fillers, solvents, catalysts, stabilizers, slip aids, rheology control agents, dispersing agents, adhesion promoters, UV absorbers, hindered amine light stabilizers, and so on. The pigment or filler may be any organic or inorganic compounds or colored materials, metallic or other inorganic flake materials such as pearlescent mica flake pigments or metallic flake pigments such as aluminum flake, and other materials of kind that the art normally includes in such coatings. Pigments and other insoluble particulate compounds such as fillers are usually used in the composition in an amount of 1% to 100%, based on the total solid weight of binder components (i.e., a pigment-to-binder ratio of 0.1 to 1). The non-flake fillers or pigments can be introduced by first forming a mill base with a dispersing resin by conventional techniques, such as sandgrinding, ball-milling, attritor grinding, two roll milling to disperse the pigments. The mill base may then be added to the coating composition.

Nonlimiting examples of catalysts that may optionally be incorporated into the curable compositions include p-toluene sulfonic acid, dinonylnaphthalene disulfonic acid, dodecylbenzenesulfonic acid, phenyl acid phosphate, monobutyl maleate, butyl phosphate, and hydroxy phosphate ester. Strong acid catalysts are often blocked, e.g. with an amine. Other catalysts that may be useful in the composition of the invention include Lewis acids, zinc salts, and tin salts, including dibutyltin oxide, dioctyltin oxide, dibutyltin dilaurate, dibutyltin diacetate, dibutyl tin dimaleate, dibutyl tin distearate, dipropyltin dioctoate and dioctyl tin oxide, aliphatic bismuth carboxylates such as bismuth ethylhexanoate, bismuth subsalicylate (having an empirical formula $C_7H_5O_4Bi$), zinc octoate, zinc naphthenate, zinc tallate, zinc carboxylates having from about 8 to 14 carbons in the carboxylate groups, and zinc acetate.

The coating compositions of the invention may be primer or topcoat compositions, including one-layer pigmented topcoat compositions as well as clearcoat and basecoat two-layer topcoat compositions. In a basecoat-clearcoat topcoat, an underlayer of a pigmented coating, the basecoat, is covered with an outer layer of a transparent coating, the clearcoat. Basecoat-clearcoat topcoats provide an attractive smooth and glossy finish and generally improved performance. The coating composition may be waterborne, solventborne, or a powder coating, which may be a dry powder or an aqueous powder slurry. Clearcoat coating compositions are transparent.

The coating composition can be applied to a substrate according to any of a number of techniques well-known in the art. These include, for example, spray coating, dip coating, roll coating, curtain coating, and the like. For automotive applications, the further coating layer or layers are preferably applied by spray coating, particularly electrostatic spray methods. Coating layers of one mil (about 25 microns) or more are usually applied in two or more coats (passes), separated by a time sufficient to allow some of the solvent or aqueous medium to evaporate, or "flash," from the applied layer. The flash may be at ambient or elevated temperatures, for example, the flash may use radiant heat. The coats as applied can be from 0.5 mil up to 3 mils dry, and a sufficient number of coats are applied to yield the desired final coating thickness.

A cured primer layer may be cured before a topcoat layer is applied. The cured primer layer may be from about 0.5 mil to about 2 mils thick, preferably from about 0.8 mils to about 1.2 mils thick.

Color-plus-clear topcoats are usually applied wet-on-wet. The compositions are applied in coats separated by a flash, as described above, with a flash also between the last coat of the color composition and the first coat the clear. The two coating layers are then cured simultaneously. Preferably, the cured basecoat layer is 0.5 to 1.5 mils thick, and the cured clear coat layer is 1 to 3 mils, more preferably 1.6 to 2.2 mils, thick.

Alternatively the primer layer and the topcoat can be applied "wet-on-wet." For example, the primer composition can be applied, then the applied layer flashed; then the topcoat can be applied and flashed; then the primer and the topcoat can be cured at the same time. Again, the topcoat can include a basecoat layer and a clearcoat layer applied wet-on-wet. The primer layer can also be applied to an uncured electrocoat coating layer, and all layers cured together.

The coating compositions described herein are preferably subjected to conditions so as to cure the coating layers. Although various methods of curing may be used, heat-curing is preferred. Generally, heat curing is effected by exposing the coated article to elevated temperatures provided primarily by radiative heat sources. Curing temperatures will vary depending on the particular binder components, however they generally range between 90° C. and 180° C. The curing time will vary depending on the particular components used, and physical parameters such as the thickness of the layers, however, typical curing times range from 15 to 60 minutes.

The invention is further described in the following examples. The examples are merely illustrative and does not in any way limit the scope of the invention as described and claimed. All parts are parts by weight unless otherwise noted.

EXAMPLE ONE

Di-functional Alkoxycarbonylamino Material

A mixture of 100 grams of a dicarbamate with an equivalent weight of 310, made according to U.S. Pat. No. 6,962,730, 0.6 g of palladium chloride, 4.3 g of cupper(II) chloride, 4.8 g of dibasic sodium phosphate, 500 g of 1-butanol is pressurized two times with 100 PSI of carbon monoxide followed by release of pressure. Then the system is pressurized with a mixture of 97% carbon monoxide and 3% oxygen to 1000 psig and heated to 80° C. for 48 hours. The reaction mixture is then allowed to cool to room temperature and the pressure is released. The reaction mixture is then filtered and the excess butanol removed by vacuum distillation (keeping the temperature below 40° C.) to obtain a product with two butoxycarbonylamino functional groups with an equivalent weight of 410 g/equ.

EXAMPLE TWO

Alkoxycarbonylamino-Functional Monomer

A mixture of 100 grams of 2-carbamate ethyl methacrylate, 1.0 g of palladium chloride, 7.2 g of cupper(II) chloride, 8.0 g of dibasic sodium phosphate, 800 g of 1-butanol butanol is pressurized two times with 100 PSI of carbon monoxide followed by release of pressure. Then the system is pressurized with a mixture of 97% carbon monoxide and 3% oxygen to 1000 psig and heated to 80° C. for 48 hours. The reaction mixture is then allowed to cool to room temperature and the pressure is released. The reaction mixture is then filtered. 0.5 g of 4-methoxy phenol is added and the excess butanol removed by vacuum distillation (keeping the temperature below 40° C. and bleeding in a small amount of oxygen) to obtain 2-butoxycarbonylamino ethyl methacrylate.

EXAMPLE THREE

Alkoxycarbonylamino Polymeric Material

In a reactor equipped to remove distillates, a mixture of 100 g of the dicarbamate with an equivalent weight of 366, made according to U.S. Pat. No. 5,336,566, 1000 g of butanol, 475 g of sodium methoxide 30% solution in methanol, 79 g of sodium methoxide and 245 g of dimethyl carbonate is heated to 95° C. for 2 hours. The reaction mixture is then cooled to room temperature and 350 g of a 30% nitric acid solution in water was added. The reaction mixture was stirred and the water layer removed. The reaction mixture was then washed two more times with 100 g of water. The solvent was then removed from the organic phase to give a mixed methyl and butyl tris(alkoxycarbonylamino) isocyanurate based polymer.

What is claimed is:

1. A curable coating composition comprising a first material having a plurality of functional groups (I)

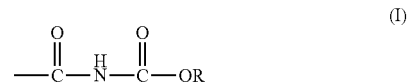

wherein each is bonded to an oxygen atom, a nitrogen atom, or a sulfur atom, wherein R is a group having 1 to 12 carbons and optionally including one or more heteroatoms selected from oxygen, nitrogen, and sulfur and a second material having a plurality of functional groups selected from the group consisting of epoxide groups, active hydrogen-containing functional groups, and activated methylene groups.

2. A curable composition according to claim 1, wherein the first material having the functional groups (I) further comprises a group (II)

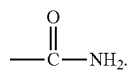
(II)

3. A curable composition according to claim 1, wherein R has 1 to 4 carbons.

4. A curable composition according to claim 1, wherein R comprises an oxygen.

5. A curable composition according to claim 1, wherein the first material comprises 2 to 8 functional groups of formula (I).

6. A curable composition according to claim 1, wherein the first material is a member selected from the group consisting of vinyl polymers, polyurethanes, polyesters, polyethers, epoxies, polyamides, polycarbonates, graft and block polymers thereof, and star polymers.

7. A curable composition according to claim 1, wherein the first material is an acrylic polymer or (meth)acrylate monomer.

8. A curable composition according to claim 1, wherein the second material is a polymer or oligomer and the first material is a compound.

9. A curable composition according to claim 1, wherein the second material is a compound and the first material is a polymer or oligomer.

* * * * *